United States Patent [19]

Kelly et al.

[11] 4,332,950
[45] Jun. 1, 1982

[54] THIAZOLIDINE-SUBSTITUTED PHENYL SULFONIC ACIDS

[75] Inventors: Charles A. Kelly, Dorchester; Frank A. Meneghini, Arlington, both of Mass.

[73] Assignee: Polaroid Corporation, Cambridge, Mass.

[21] Appl. No.: 239,356

[22] Filed: Mar. 2, 1981
(Under 37 CFR 1.47)

[51] Int. Cl.³ ............................................ C07D 277/04
[52] U.S. Cl. ...................................... 548/146; 260/147
[58] Field of Search .......................................... 548/146

[56] References Cited
U.S. PATENT DOCUMENTS 3,719,489 3/1973 Cieciuch et al. ...................... 96/290
4,098,783 7/1978 Cieciuch et al. ..................... 260/147

OTHER PUBLICATIONS

Westland et al.; J. Med. Chem., vol. 16, pp. 328–331 (1973).
Weil et al.; Chem. Ber., vol. 55, pp. 301–305 (1922).
Kirker OPPI Briefs, vol. 12, Nos. 3–4, (Jun.–Aug. 1980) pp. 246–249.

*Primary Examiner*—Mary Lee
*Attorney, Agent, or Firm*—Sybil A. Campbell

[57] ABSTRACT

This invention relates to certain 3-(thiazolidin-2'-yl)-4-hydroxy-phenyl sulfonic acids and to a method of converting said sulfonic acids to the corresponding sulfonyl chlorides by reacting said acid with neat thionyl chloride or with thionyl chloride in a chlorinated hydrocarbon. In another embodiment, the 3-(thiazolidin-2'-yl)-4-hydroxy-phenyl sulfonic acid is synthesized, without isolating intermediates, starting with the sulfonation of salicylaldehyde and then forming the 3-(thiazolidin-2'-yl) substituent.

16 Claims, No Drawings

THIAZOLIDINE-SUBSTITUTED PHENYL SULFONIC ACIDS

FIELD OF THE INVENTION

This invention relates to 3-(thiazolidin-2'-yl)-4-hydroxy-phenyl sulfonic acids, to their synthesis and to their use in the preparation of the corresponding sulfonyl chlorides.

BACKGROUND OF THE INVENTION

U.S. Pat. No. 3,719,489 describes and claims photographic processes employing certain potographically inert compounds which are capable of undergoing cleavage in the presence of the imagewise distribution of silver ions made available during processing of a silver halide emulsion to liberate a reagent, such as, a photographically active reagent or a dye in an imagewise distribution corresponding to that of said silver ions. In one embodiment disclosed therein, color images are produced by using as the photographically inert compounds, color-providing compounds which are substantially non-diffusible in the photographic processing composition but capable of undergoing cleavage in the presence of the imagewise distribution of silver ions and/or soluble silver complex made available in the undeveloped and partially developed areas of a silver halide emulsion as a function of development to liberate a more mobile and diffusible color-providing moiety in an imagewise distribution corresponding to the imagewise distribution of said ions and/or said complex. The subsequent formation of a color image is the result of the differential in diffusibility between the parent compound and liberated color-providing moiety whereby the imagewise distribution of the more diffusible color-providing moiety released in the undeveloped and partially developed areas is free to transfer.

Compounds disclosed as useful in liberating a reagent in the presence of said silver ions and/or silver complex are sulfur-nitrogen compounds containing the group

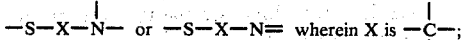

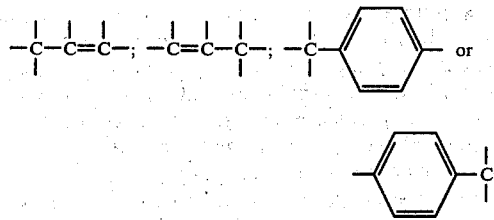

These 1,3-sulfur-nitrogen compounds may be linear or cyclic in structure, and in a particularly preferred embodiment are thiazolidine compounds, such as, compounds which comprise a dye radical having the chromophoric system of an azo, anthraquinone, phthalocyanine or other dye and a thiazolidin-2'-yl moiety which may be bonded directly to the dye radical or through an appropriate linking group.

U.S. Pat. No. 4,098,783, a continuation-in-part of Ser. No. 465,694, now abandoned, which is a division of said U.S. Pat. No. 3,719,489 discloses that dyes substituted with a thiazolidin-2'-yl moiety may be synthesized by condensing a dye possessing an aldehyde group with a 2-aminoethanethiol, or rather than forming the thiazolidin-2-yl moiety as the final step in the synthesis, an intermediate possessing an aldehyde group may be condensed with the selected 2-aminoethanethiol and the condensation product then reacted with the appropriate molecule or molecules to yield the final dye product. For example, an intermediate comprising a linking group substituted with a thiazolidin-2'-yl moiety may be synthesized from a selected aldehyde in several steps including the condensation with a 2-aminoethanethiol and the linking group then reacted as an amine with a dye radical possessing, e.g., a sulfonyl chloride substituent or it may be reacted as a sulfonyl chloride with a dye radical possessing an amino substituent.

The sodium salt of 5-sulfosalicylaldehyde and its synthesis from 5-sulfosalicy lic acid has been reported by H. Weil and K. Brimmer, Chem. Ber., 55, p. 302 (1922). In the procedure described by these authors, 5-sulfosalicylaldehyde was prepared by reducing sulfosalicy lic acid with sodium amalgam, treating the reduction product with aniline to precipitate it as a Schiff base, and after strongly acidifying with hydrochloric acid, isolating the sulfonated aldehyde as its sodium salt using sodium chloride. The preparation of various sulfo-substituted compounds by the sulfonation of aromatic hydrocarbons with concentrated sulfuric acid, fuming sulfuric acid and other sulfonation reagents also is known. G. W. Kirker, OPPI Briefs, Vol. 12, Nos. 3–4 (June-August 1980) pp. 246–249 has reported the synthesis of the sodium salt of 5-sulfosalicylaldehyde by sulfonation of salicylaldehyde with 95% surfuric acid at 40° C. followed by careful dilution of the reaction mixture with water, neutralization with sodium carbonate and isolation of the salt after reducing the volume of the reaction mixture by about one-half.

Also, it is known that sulfo-substituted compounds, either as the free sulfonic acid or in the form of a salt, may be converted to the corresponding sulfonyl chloride by treating with phosphorus chlorides or with an excess of thionyl chloride. Though these reagents have been generally useful in these and in various other conversion reactions to give the desired chlorides, some exceptions have been noted. For example, Roger D. Westland et al., J. Med. Chem., Vol. 16, No. 4, p. 328 (1973) report that "3-Thiazolidinealkanol hydrochlorides IV suspended in THF were readily converted (SOCl$_2$) to alkyl chlorides V." but that "Other solvents or lack of solvent led to decomposition of the sensitive thiazolidine ring."

SUMMARY OF THE INVENTION

According to the present invention, it has been found quite unexpectedly that a 3-(thiazolidin-2'-yl)-4-hydroxy-phenyl sulfonic acid can be reacted as its hydrochloride salt with neat thionyl chloride or with thionyl chloride in a chlorinated hydrocarbon to give the corresponding sulfonyl chloride without decomposition of the thiazolidin-2'-yl moiety. Also, it has been discovered that the said sulfonic acid-hydrochloride salt can be synthesized from salicylaldehyde without isolating the 5-sulfosalicylaldehyde and other intermediates formed en route to the 3-(thiazolidin- 2'-yl)-4-hydroxy-phenyl sulfonic acid hydrochloride salt. By proceeding in this manner, the problems associated with isolating the salt of the 5-sulfosalicylaldehyde from the sulfuric acid reaction mixture before converting the aldehyde into the thiazolidinyl substituent are obviated. Moreover, the subject process lends itself to the production of the said sulfonic acid hydrochloride on a large scale.

It is, therefore, the primary object of the present invention to provide a method of synthesizing 3-(thiazolidin-2'-yl)-4-hydroxy-phenyl sulfonyl chlorides.

It is another object of the present invention to provide a method of synthesizing 3-(thiazolidin-2'-yl)-4-hydroxy phenyl sulfonic acids and their hydrochloride salts useful in the synthesis of said sulfonyl chlorides.

It is a further object of the present invention to provide certain thiazolidinyl-substituted phenyl sulfonic acids.

Other objects of this invention will in part be obvious and will in part appear hereinafter.

The invention accordingly comprises the processes involving the several steps and the relation and order of one or more of such steps with respect to each of the others, and the product possessing the features, properties and the relation of elements, which are exemplified in the following detailed disclosure, and the scope of the application of which will be indicated in the claims.

For a fuller understanding of the nature and objects of the present invention, reference should be had to the following detailed description.

DESCRIPTION OF THE PREFERRED EMBODIMENTS

In one embodiment, the method of the present invention comprises reacting a 3-(thiazolidin-2'-yl)-4-hydroxy-phenyl sulfonic acid, preferably as its hydrochloride salt, with an excess over equimolar amounts of (i) neat thionyl chloride or (ii) thionyl chloride in a chlorinated hydrocarbon preferably in the presence of a catalytic amount of N,N-dimethylformamide to yield the corresponding 3-(thiazolidin-2'-yl)-4-hydroxy-phenyl sulfonyl chloride.

In another embodiment of the present invention, the 3-(thiazolidin-2'-yl)-4-hydroxy-phenyl sulfonic acid. hydrochloride employed in the aforementioned method is prepared by (a) reacting salicylaldehyde with fuming sulfuric acid to yield 5-sulfosalicylaldehyde;

(b) neutralizing said sulfuric acid reaction mixture with an alkanol solution of sodium hydroxide to yield the sodium salt of said 5-sulfosalicylaldehyde;

(c) reacting said sodium salt of 5-sulfosalicylaldehyde in said alkanol solution with a 2-aminoethanethiol wherein said 2-amino group has one replaceable hydrogen atom or its hydrochloride salt to yield the corresponding 3-(thiazolidin-2'-yl)-4-hydroxy-phenyl sodium sulfonate;

(d) removing sodium sulfate and unreacted 2-aminoethanethiol from said alkanol solution containing said 3-(thiazolidin-2'-yl)-4-hydroxy-phenyl sodium sulfonate;

(e) then acidifying said alkanol solution containing said 3-(thiazolidin-2'-yl)-4-hydroxy-phenyl sodium sulfonate with concentrated hydrochloric acid to yield the corresponding 3-(thiazolidin-2'-yl)-4-hydroxy-phenyl sulfonic acid, as its hydrochloride salt; and isolating said hydrochloride salt.

The reaction scheme of the present method including the synthesis of the subject 3-(thiazolidin-2'-yl)-4-hydroxy-phenyl sulfonic acid hydrochlorides in the above manner is illustrated below wherein 1,1-dimethyl-2-n-octadecylamino-ethanethiol is employed as the 2-aminoethanethiol for condensation with the aldehyde group of the sulfonated salicylaldehyde to yield the corresponding 3-(5',5'-dimethyl-3'-n-octadecyl-thiazolidin-2'-yl) compound.

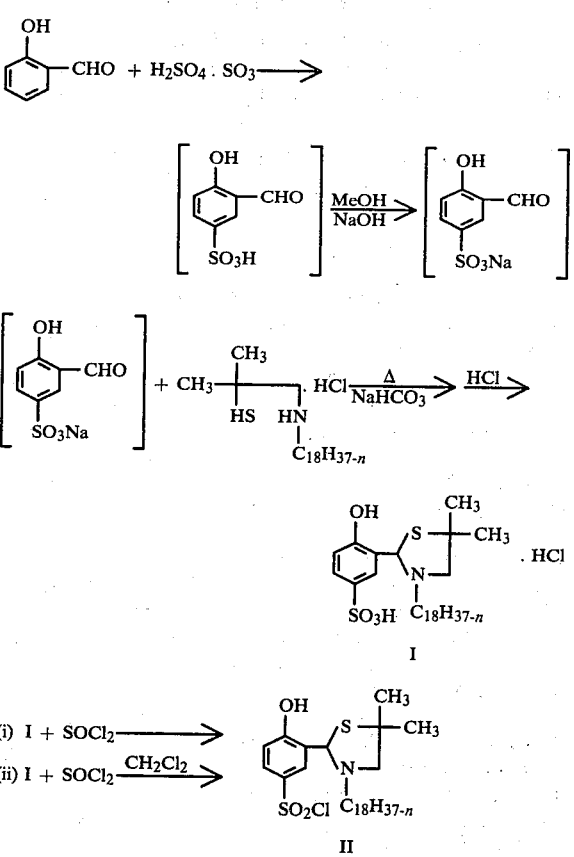

It will be appreciated that the sulfonyl chloride, II, can be readily converted to its hydrochloride salt in a conventional manner, for example, by treating with gaseous hydrogen chloride. Because of the free flowing properties of the salt, it may be desirable to convert the product to its hydrochloride for ease of handling.

In preparing the said sulfonyl chlorides according to the present invention, the sulfonic acid-hydrochloride is reacted with an excess over equimolar amounts of neat thionyl chloride or thionyl chloride in a chlorinated hydrocarbon, preferably in the presence of a catalytic amount of N,N-dimethylformamide (DMF). When the reaction is conducted in neat thionyl chloride, this reagent generally is used in large excess over equimolar amounts since it also functions as the reaction solvent. When the reaction is conducted in a chlorinated hydrocarbon, usually about 2 molar equivalents of thionyl chloride are employed which amount may vary up to about 5 molar equivalents. Ordinarily, the reaction with thionyl chloride is conducted at room temperature, and the chlorinated hydrocarbon is methylene chloride.

The 3-(thiazolidin-2'-yl)-4-hydroxy-phenyl sulfonic acid hydrochloride used as the starting material for reaction with the thionyl chloride is prepared without isolating intermediates by reacting the salicylaldehyde with fuming sulfuric acid (25-45% SO₃) to give 5-sulfosalicylaldehyde. Usually, the fuming sulfuric acid is employed in a quantity sufficient to provide a slight excess of SO₃ over equimolar amounts of the starting aldehyde. The reaction is exothermic, usually reaching a temperature of 70° to 75° C. and may be cooled to lower temperatures of 40° to 50° C., if desired.

The reaction mixture comprising the 5-sulfosalicylaldehyde is neutralized by admixture with an alkanol solution, usually an ethanol or methanol solution of sodium hydroxide to give the sodium salt of the 5-sulfosalicylaldehyde. Preferably, the neutralization is carried out in the presence of a small amount of water, since in the absence of water the neutralization proceeds very slowly. It has been observed that the reaction mixture appears to be neutralized when the original red dispersion has disappeared and turned yellow.

The sodium salt of the 5-sulfosalicylaldehyde in the alkanol solution is then refluxed with a 2-aminoethanethiol wherein said 2-amino group has one replaceable hydrogen atom or its hydrochloride salt to give the corresponding 3-(thiazolidin-2'-yl)-4-hydroxy-phenyl sodium sulfonate. Where the hydrochloride is employed, the salt is neutralized. For example, the reaction is conducted in the presence of sodium bicarbonate which is used in at least equimolar amounts based on the aminoethanethiol hydrochloride, or the amount of sodium hydroxide used in the preceeding neutralization step may be adjusted to include at least the stoichiometric amount necessary for reacting with the hydrochloride. As to the latter reagent, it will be appreciated that the salt form is used as a matter of convenience, and where the amine base is employed, the use of sodium bicarbonate or additional sodium hydroxide for freeing the HCl, of course, is unnecessary. The ratio of aminoethanethiol reagent to salicylaldehyde may range between about 0.5–1.0:1, but it may be desirable to alter the amount of aminoethanethiol to increase yields. Also, it may be desirable to conduct the reaction in an inert atmosphere, for example under a blanket of nitrogen.

After formation of the thiazolidinyl-substituted compound, sodium sulfate and unreacted 2-aminoethanethiol are removed from the alkanol solution. Depending upon the compound, the solution may be filtered to remove sodium bicarbonate, sodium sulfate and some unreacted aminoethanethiol and then extracted with hexane to remove any remaining unreacted aminoethanethiol and disulfide. For more efficient extraction, the pH selected should ensure that the aminoethanethiol and/or disulfide exists as a free base.

The alkanol solution is then acidified with concentrated hydrochloric acid to convert the 3-(thiazolidin-2'-yl)-4-hydroxy-phenyl sodium sulfonate to the corresponding 3-(thiazolidin-2'-yl)-4-hydroxy-phenyl sulfonic acid-hydrochloride. The hydrochloride salt is then isolated by reducing the volume of acidified alkanol solution, quenching with water and collecting the precipitate. Though the sulfonic acid may be isolated and reacted with the thionyl chloride as the free base, the hydrochloride salt is employed as a matter of convenience because of ease of isolation and handling.

Any 2-aminoethanethiol or its hydrochloride salt may be employed in the foregoing synthesis provided that the 2-amino group of the compound has one replaceable hydrogen atom. Typical 2-aminoethanethiols that may be employed are those having the formula

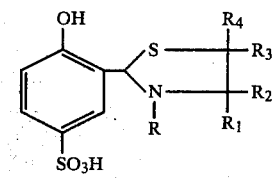

wherein $R_1$, $R_2$, $R_3$ and $R_4$ each are selected from hydrogen, phenyl and alkyl containing 1 to 20 carbon atoms and R is selected from alkyl containing 1 to 20 carbon atoms, usually 10 to 20 carbon atoms, phenyl-substituted alkyl wherein said alkyl contains 1 to 20 carbon atoms, and phenyl. The alkyl and phenyl groups comprising R, $R_1$, $R_2$, $R_3$ and $R_4$ may be unsubstituted or substituted with a group non-reactive with thionyl chloride, such as, alkoxy, alkyl, alkenyl and N,N-dialkylamino. Such compounds are known in the art and may be synthesized in various ways, for example, by the mercaptoethylation of amines and ammonia with episulfides as disclosed and claimed in U.S. Pat. No. 3,919,277 of Roberta R. Luhowy and Frank A. Meneghini.

Typical 3-(thiazolidin-2'-yl)-4-hydroxy-phenyl sulfonic acids of the present invention may be represented by the formula

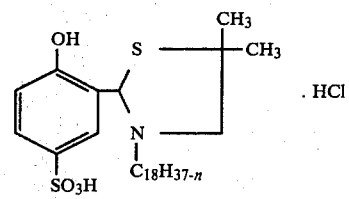

wherein R, $R_1$, $R_2$, $R_3$ and $R_4$ have the same meaning given above. It will be appreciated that the subject sulfonic acids also include the corresponding salts, particularly the hydrochloride.

The following examples are given to further illustrate the present invention and are not intended to limit the scope thereof.

EXAMPLE 1

Preparation of the compound having the formula

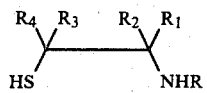

To a stirring solution of 51.60 g (~0.2 mole of SO₃) of fuming sulfuric acid was added 19.52 g (0.16 mole) of salicylaldehyde. The salicylaldehyde was added at a rate to maintain a temperature of 70°–75° C. After the addition of the aldehyde, the reaction mixture was stirred an additional 1.5 hours yielding a viscous red-brown solution comprising 5-sulfosalicylaldehyde.

This solution was placed in a dropping funnel and added dropwise to 40.4 g (1.0 mole) of sodium hydroxide in 300 ml of absolute methanol. The original sulfonation flask was rinsed out with 20 ml of water and also added dropwise. Upon addition of the aqueous solution, the mixture produced a slight exotherm and neutralization followed. The mixture was vigorously stirred for 2.5 hours after which there was a white solid comprising the sodium salt of 5-sulfosalicylaldehyde suspended in a yellow liquid. The pH of this dispersion was 8.5 to 9.0.

To this vigorously stirred dispersion was added 37.92 g (0.092 mole) of 1,1-dimethyl 2-n-octadecylaminoethanethiol hydrochloride and 8.10 g (0.092 mole) of sodium bicarbonate. The resulting mixture was refluxed four hours. TLC showed unreacted sulfosalicylaldehyde and unreacted aminoethanethiol, so an additional 8.10 g (0.092 mole) of sodium bicarbonate was added and the reaction refluxed for an additional eight hours. The pH was 6.5. TLC still showed the reaction to be incomplete so an additional 8.10 g of sodium bicarbonate was added (note: total amount of sodium bicarbonate used was 24.3 g), and the reaction refluxed an additional four hours, after which the solution was filtered hot. The solid collected was washed with 500 ml absolute methanol which was combined with the filtrate.

The yellow filtrate containing the sodium salt of 3-(5',5'-dimethyl-3'-n-octadecyl-thiazolidin-2'-yl)-4-hydroxy-phenyl sulfonic acid was then adjusted to pH > 12 with sodium hydroxide and extracted with 400 ml of hexane leaving an orange methanolic solution.

This methanolic solution was then acidified to pH ≦ 2 with conc. hydrochloric acid and concentrated in vacuo to a volume of about 100 ml. This solution was then quenched into one liter of water with vigorous stirring. The precipitate that formed was collected by filtration, dried in vacuo at 60° C. for four hours yielding a very light orange solid. This solid was triturated with 500 ml of absolute methanol, filtered and the filtrate treated as above to give 23.6 g of the title compound as an almost colorless solid. The yield based on the limiting reagent, namely, the 1,1-dimethyl-2-n-octadecylaminoethanethiol.HCl was 42.5% by weight.

EXAMPLE 2

Preparation of the compound having the formula

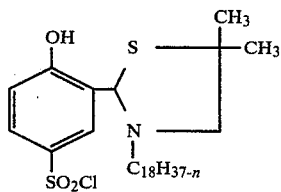

6.18 g (0.059 mole) of thionyl chloride was added to 10.0 g (0.0173 mole) of 3-(5',5'-dimethyl-N-n-octadecyl-thiazolidin-2'-yl)-4-hydroxy-phenyl sulfonic acid.HCl in 500 ml of dichloromethane. To this stirring solution was added 3 drops of N,N-dimethylformamide. The reaction mixture was allowed to stir at room temperature overnight. TLC showed little or no sulfonyl chloride formation ($R_f$= 1 in CHCl$_3$) so an additional 4.11 g (0.0346 mole) of thionyl chloride and 0.5 ml of N,N-dimethylformamide were added to the reaction mixture. This solution was allowed to stir at room temperature for 18 hours. TLC showed predominately sulfonyl chloride to be present. The reaction mixture was quenched with water (2×100 ml), stirred vigorously, partitioned and the organic layer dried over sodium sulfate. The sodium sulfate was removed by filtration and the organic phase evaporated in vacuo leaving a yellow oil. The oil was triturated with petroleum ether (100 ml) and the insoluble material removed by filtration. This insoluble material was triturated with petroleum ether (2×100 ml) and the petroleum ether filtrates combined and evaporated in vacuo yielding (6.92 g) of the title compound as a very light yellow solid. (71.5% by weight yield)

| Analysis for | C | H | N | S | Cl |
|---|---|---|---|---|---|
| Calculated | 62.17 | 9.00 | 2.49 | 11.44 | 6.33 |
| Found | 62.76 | 9.05 | 2.45 | 11.80 | 6.12 |

The compound of Example 2 was converted to its hydrochloride salt as follows:

The compound obtained above was dissolved in 2.5% dichloromethane/petroleum ether solution and dry HCl gas was bubbled through the solution slowly yielding a white precipitate. The precipitate was filtered and air dried to give the said hydrochloride salt as a white solid in quantitative yield.

EXAMPLE 3

Preparation of the compound having the formula

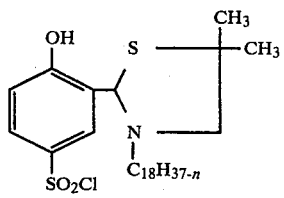

The hydrochloride salt of 3-(5',5'-dimethyl-N-n-octadecyl-thiazolidin-2'-yl)-4-hydroxy-phenyl sulfonic acid (0.60 g; 1.04 mmoles) and 1 drop of N,N-dimethylformamide were stirred at room temperature for 18 hours in 2 ml of thionyl chloride under a blanket of nitrogen. The reaction mixture was then quenched onto crushed ice yielding a light yellow solid comprising 3-(5',5'-dimethyl-N-n-octadecyl-thiazolidin-2'-yl)-4-hydroxy-phenyl sulfonyl chloride which was collected by vacuum filtration.

As mentioned previously, the sulfonyl chlorides prepared by the subject method are useful as intermediates in the synthesis of photographic image dye-providing materials. For instance, they may be employed as intermediates in the preparation of thiazolidine-substituted dye image-providing materials as described in aforementioned U.S. Pat. No. 4,098,783. For this purpose, they may be reacted with a dye substituted with an amino group to yield the image dye-providing material, or they may be reacted with an alkylene diamine and the reaction product reacted with a dye substituted with, e.g., a —COCl or —SO$_2$Cl group to give the image dye-providing material. As an example, the compound having the formula

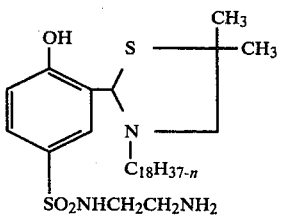

Compound A was prepared as follows:

The yellow solid obtained in Example 3 was dissolved in 10 ml of tetrahydrofuran and added slowly to 4 ml (3.6 g; 59.8 mmoles) of ethylenediamine, and the resulting reaction mixture was stirred at room temperature for 20 minutes. The tetrahydrofuran was then evaporated in vacuo yielding a yellow gum which was dissolved in ethyl acetate and subsequently extracted with saturated bicarbonate solution; 1 N HCl and brine. The organic phase was then dried over sodium sulfate. The sodium sulfate was filtered off and the filtrate was evaporated in vacuo yielding 0.37 g of crude product. The crude material was chromatographed on $SiO_2$ using 20% methanol/chloroform as the eluent to give 0.21 g (0.36 mmoles) of the title compound, which was confirmed by TLC and nmr. (yield 34.6% by weight).

The dihydrochloride salt of the above compound was prepared as follows:

To 80 ml of dry dichloromethane stirred at $-5°$ to $0°$ C. was added 9.04 g (150 mmoles) of ethylenediamine. To the solution was added 2.00 g (3.30 mmoles) of 3-(5',5'-dimethyl-N-n-octadecyl-thiazolidin-2'-yl)-4-hydroxy-phenyl sulfonyl chloride.hydrochloride in 10 ml of dichloromethane using an addition funnel. The sulfonyl chloride was added at a rate such that the temperature remained between about 0° and 5° C. The mixture was then stirred at 0° C. for 1.5 hours. It was then extracted with 100 ml (×2) of 1 N HCl, 100 ml of water, and 100 ml of brine. The organic layer was dried over magnesium sulfate. The magnesium sulfate was removed by filtration, and 70 ml of hexane was added to the stirring dichloromethane solution. Dry HCl was slowly bubbled through the solution until no more was absorbed. The solvent was evaporated in vacuo to dryness yielding the title compound as a pale yellow solid: 1.92 g (2.80 mmoles); 85.4% by weight yield.

It will be appreciated that this sulfonamide may then be reacted with a dye possessing a —COCl or —$SO_2Cl$ group to give the image dye-providing material. As an illustration, 280 mgs of Compound A and 190 mgs (one equivalent) of the yellow dye of the formula

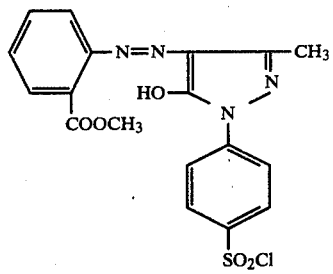

were combined in pyridine and allowed to stir overnight. The pyridine was evaporated, dilute HCl added, and the residue triturated and filtered. The residue was taken up in chloroform, dried over sodium sulfate and concentrated. The solution was applied to a Florosil column (chloroform) and eluted with chloroform and 20% acetone/chloroform to give 210 mgs of the desired image dye-providing material of the formula

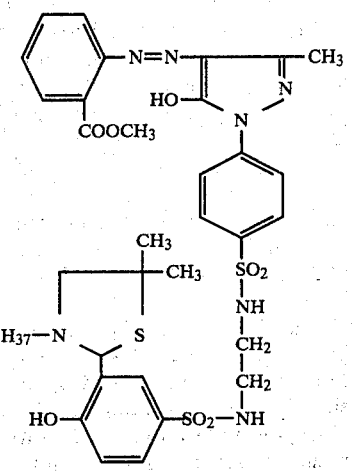

which was confirmed by nmr ($CDCl_3$).

Thiazolidine-substituted 4-hydroxy-phenyl sulfonyl chlorides, such as those prepared above, form the subject matter of copending U.S. patent application Ser. No. 239,358 of Myron S. Simon filed concurrently herewith.

Since certain changes may be made in the herein described subject matter without departing from the scope of the invention herein involved, it is intended that all matter contained in the above description and examples be interpreted as illustrative and not in a limiting sense.

What is claimed is:

1. A method which comprises reacting the hydrochloride salt of a 3-(thiazolidin-2'-yl)-4-hydroxy-phenyl sulfonic acid with an excess over equimolar amounts of (i) neat thionyl chloride or (ii) thionyl chloride in a chlorinated hydrocarbon to yield the corresponding 3-(thiazolidin-2'-yl)-4-hydroxy-phenyl sulfonyl chloride.

2. A method as defined in claim 1 wherein said 3-(thiazolidin-2'-yl)-4-hydroxy-phenyl sulfonic acid hydrochloride salt is reacted with neat thionyl chloride in a large excess over equimolar amounts.

3. A method as defined in claim 1 wherein one molar equivalent of 3-(thiazolidin-2'-yl)-4-hydroxy-phenyl sulfonic acid hydrochloride salt is reacted with about 2 to 5 molar equivalents of thionyl chloride in a chlorinated hydrocarbon.

4. A method as defined in claim 1 wherein said reaction is conducted in the presence of a catalytic amount of N,N-dimethylformamide.

5. A method as defined in claim 1 wherein said hydrochloride salt is 3-(5',5'-dimethyl-3'-n-octadecylthiazolidin-2'-yl)-4-hydroxy-phenyl sulfonic acid.HCl.

6. A method as defined in claim 1 which includes the additional step of converting said 3-(thiazolidin-2'-yl)-4-hydroxy-phenyl sulfonyl chloride to its hydrochloride salt by treating with hydrogen chloride.

7. A method as defined in claim 1 which includes the additional steps of synthesizing said 3-(thiazolidin-2'-yl)-4-hydroxy-phenyl sulfonic acid hydrochloride salt without isolation of intermediates by (a) reacting salicylaldehyde with fuming sulfuric acid to yield 5-sulfosalicylaldehyde;

(b) neutralizing said sulfuric acid reaction mixture with an alkanol solution of sodium hydroxide to yield the sodium salt of said 5-sulfosalicylaldehyde;

(c) reacting said sodium salt of 5-sulfosalicylaldehyde in said alkanol solution with a 2-aminoethanethiol wherein said 2-amino group has one replaceable hydrogen atom or its hydrochloride salt to yield the corresponding 3-(thiazolidin-2'-yl)-4-hydroxy-phenyl sodium sulfonate;

(d) removing sodium sulfate and unreacted 2-aminoethanethiol from said alkanol solution containing said 3-(thiazolidin-2'-yl)-4-hydroxy-phenyl sodium sulfonate;

(e) then acidifying said alkanol solution containing said 3-(thiazolidin-2'-yl)-4-hydroxy-phenyl sodium sulfonate with concentrated hydrochloric acid to yield the corresponding 3-(thiazolidin-2'-yl)-4-hydroxy-phenyl sulfonic acid, as its hydrochloride salt; and isolating said hydrochloride salt.

8. A method of synthesizing a 3-(thiazolidin-2'-yl)-4-hydroxy-phenyl sulfonic acid hydrochloride salt without isolation of intermediates which comprises (a) reacting salicylaldehyde with fuming sulfuric acid to yield 5-sulfosalicylaldehyde;

(b) neutralizing said sulfuric acid reaction mixture with an alkanol solution of sodium hydroxide to yield the sodium salt of said 5-sulfosalicylaldehyde;

(c) reacting said sodium salt of 5-sulfosalicylaldehyde in said alkanol solution with a 2-aminoethanethiol wherein said 2-amino group has one replaceable hydrogen atom or its hydrochloride salt to yield the corresponding 3-(thiazolidin-2'-yl)-4-hydroxy-phenyl sodium sulfonate;

(d) removing sodium sulfate and unreacted 2-aminoethanethiol from said alkanol solution containing said 3-(thiazolidin-2'-yl)-4-hydroxy-phenyl sodium sulfonate;

(e) then acidifying said alkanol solution containing said 3-(thiazolidin-2'-yl)-4-hydroxy-phenyl sodium sulfonate with concentrated hydrochloric acid to yield the corresponding 3-(thiazolidin-2'-yl)-4-hydroxy-phenyl sulfonic acid, as its hydrochloride salt; and isolating said hydrochloride salt.

9. A method as defined in claim 8 wherein said sodium salt of 5-sulfosalicylaldehyde is reacted in step (c) with a 2-aminoethanethiol hydrochloride salt in the presence of sodium bicarbonate.

10. A method as defined in claim 9 wherein said 2-aminoethanethiol hydrochloride salt is 1,1-dimethyl-2-n-octadecylaminoethanethiol.HCl and said sodium bicarbonate is used in at least equimolar amounts based on said aminoethanethiol.HCL.

11. A method as defined in claim 8 wherein said 3-(thiazolidin-2'-yl)-4-hydroxy-phenyl sodium sulfonate of step (d) is 3-(5',5'-dimethyl-3'-n-octadecyl-thiazolidin-2'-yl)-4-hydroxy-phenyl sodium sulfonate.

12. A method as defined in claim 11 wherein said sodium sulfate and unreacted 2-aminoethanethiol are removed from said alkanol solution containing said 3-(5',5'-dimethyl-3'-n-octadecyl-thiazolidin-2'-yl)-4-hydroxy-phenyl sodium sulfonate by filtration followed by extraction with hexane.

13. A compound of the formula

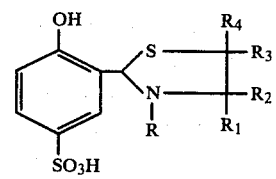

wherein R is alkyl, phenyl-substituted alkyl or phenyl and $R_1$, $R_2$, $R_3$ and $R_4$ each are selected from hydrogen, phenyl and alkyl.

14. A compound as defined in claim 13 wherein R is alkyl.

15. A compound as defined in claim 13 wherein $R_3$ and $R_4$ are methyl and $R_1$ and $R_2$ are hydrogen.

16. The compound

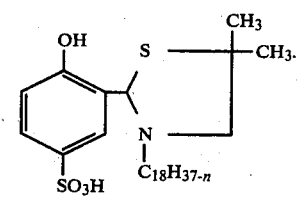

* * * * *